United States Patent
Slaikeu et al.

(10) Patent No.: US 6,231,590 B1
(45) Date of Patent: *May 15, 2001

(54) BIOACTIVE COATING FOR VASO-OCCLUSIVE DEVICES

(75) Inventors: Paul C. Slaikeu, Hayward; Joseph C. Eder, Los Altos, both of CA (US); James J. Barry, Marlborough, MA (US); Michael P. Wallace, Pleasanton; Robert M. Abrams, Sunnyvale, both of CA (US)

(73) Assignee: Scimed Life Systems, Inc., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/352,188

(22) Filed: Jul. 12, 1999

Related U.S. Application Data

(63) Continuation-in-part of application No. 09/189,540, filed on Nov. 10, 1998.

(51) Int. Cl.$^7$ ................................................. A61B 17/00
(52) U.S. Cl. .............................................................. 606/200
(58) Field of Search ..................................... 606/191, 190, 606/198, 108, 151, 1, 195, 200; 623/1, 12

(56) References Cited

U.S. PATENT DOCUMENTS

| | | |
|---|---|---|
| 3,526,005 | 9/1970 | Bokros et al. . |
| 3,847,652 | 11/1974 | Fletcher et al. . |
| 3,952,334 | 4/1976 | Bokros et al. . |
| 4,038,703 | 8/1977 | Bokros . |
| 4,164,045 | 8/1979 | Bokros et al. . |
| 4,300,244 | 11/1981 | Bokros . |
| 4,638,803 | 1/1987 | Rand . |
| 4,739,768 | 4/1988 | Engelson . |
| 4,762,128 | 8/1988 | Rosenbluth . |
| 4,768,507 | 9/1988 | Fischell et al. . |
| 4,820,298 | 4/1989 | Leveen et al. . |
| 4,871,366 | 10/1989 | von Recum et al. . |
| 4,994,069 | 2/1991 | Ritchart et al. . |
| 5,015,253 | 5/1991 | MacGregor . |
| 5,037,377 | 8/1991 | Alonso . |
| 5,095,917 | 3/1992 | Vancaillie . |
| 5,122,136 | 6/1992 | Guglielmi et al. . |
| 5,163,958 | 11/1992 | Pinchuk . |
| 5,192,301 | 3/1993 | Kamiya et al. . |
| 5,192,311 | 3/1993 | King et al. . |
| 5,226,911 | 7/1993 | Chee et al. . |
| 5,234,437 | 8/1993 | Sepetka . |
| 5,250,071 | 10/1993 | Palermo . |

(List continued on next page.)

FOREIGN PATENT DOCUMENTS

| | | |
|---|---|---|
| 196 47 280 | 10/1997 | (DE) . |
| WO 98/36784 | 8/1998 | (WO) . |

OTHER PUBLICATIONS

Dawson, R.C. et al. (Jan. 1995) "Treatment of experimental aneurysms using collagen–coated microcoils" *Neurosurgery* 36(1):133–140.

Dawson, R.C. et al. (May 1996) "Histologic effects of collagen–filled interlocking detachable coils in the ablation of experimental aneurysms in swine" *AJNR* 17:853–858.

*Primary Examiner*—Gary Jackson
*Assistant Examiner*—Vikki Hoa Trinh
(74) *Attorney, Agent, or Firm*—Morrison & Foerster, LLP

(57) ABSTRACT

This is a medical device for forming an embolism within the vasculature of a patient. More particularly, it is a vaso-occlusion device at least partially coated with a bioactive agent, a collagenous material, or a collagenous coating optionally containing or coated with other bioactive agents. A highly flexible vaso-occlusive device coated with such materials also forms a variation of the invention.

48 Claims, 1 Drawing Sheet

U.S. PATENT DOCUMENTS

| | | |
|---|---|---|
| 5,261,916 | 11/1993 | Engelson . |
| 5,304,194 | 4/1994 | Chee et al. . |
| 5,304,195 | 4/1994 | Tywford et al. . |
| 5,310,407 | 5/1994 | Casale . |
| 5,312,415 | 5/1994 | Palermo . |
| 5,350,397 | 9/1994 | Palermo et al. . |
| 5,354,295 | 10/1994 | Guglielmi et al. . |
| 5,382,259 | 1/1995 | Phelps et al. . |
| 5,382,260 | 1/1995 | Dormandy, Jr. et al. . |
| 5,383,897 | 1/1995 | Wholey . |
| 5,403,278 | 4/1995 | Ernst et al. . |
| 5,417,708 | 5/1995 | Hall et al. . |
| 5,423,849 | 6/1995 | Engelson et al. . |
| 5,443,478 | 8/1995 | Purdy . |
| 5,522,822 | 6/1996 | Phelps et al. . |
| 5,527,338 | 6/1996 | Purdy . |
| 5,536,274 | 7/1996 | Neuss . |
| 5,549,624 | 8/1996 | Mirigian et al. . |
| 5,554,181 | 9/1996 | Das . |
| 5,578,075 | 11/1996 | Dayton . |
| 5,607,445 | 3/1997 | Summers . |
| 5,618,229 | 4/1997 | Khosravi et al. . |
| 5,624,461 | 4/1997 | Mariant . |
| 5,639,277 | 6/1997 | Mariant et al. . |
| 5,643,318 | 7/1997 | Tsukernik et al. . |
| 5,645,082 | 7/1997 | Sung et al. . |
| 5,645,558 | 7/1997 | Horton . |
| 5,649,949 | 7/1997 | Wallace et al. . |
| 5,649,951 | 7/1997 | Davidson . |
| 5,658,308 | 8/1997 | Snyder . |
| 5,669,931 | 9/1997 | Kupiecki et al. . |
| 5,685,322 | 11/1997 | Sung et al. . |
| 5,690,666 | 11/1997 | Berenstein et al. . |
| 5,690,671 * | 11/1997 | McGurk et al. .................. 606/200 |
| 5,700,258 | 12/1997 | Mirigian et al. . |
| 5,704,910 | 1/1998 | Humes . |
| 5,718,711 | 2/1998 | Berenstein et al. . |
| 5,725,567 | 3/1998 | Wolff et al. . |
| 5,733,294 | 3/1998 | Forber et al. . |
| 5,743,905 | 4/1998 | Eder et al. . |
| 5,749,894 | 5/1998 | Engleson . |
| 5,792,154 | 8/1998 | Doan et al. . |
| 5,797,953 | 8/1998 | Tekulve . |
| 5,824,049 | 10/1998 | Ragheb et al. . |
| 5,827,327 | 10/1998 | McHaney et al. . |
| 5,830,230 | 11/1998 | Berryman et al. . |
| 5,837,008 | 11/1998 | Berg et al. . |
| 5,980,550 * | 11/1999 | Edger et al. .................. 606/191 |
| B1 4,739,768 | 11/1994 | Engelson . |
| B2 4,739,768 | 10/1995 | Engelson . |

* cited by examiner

BIOACTIVE COATING FOR VASO-OCCLUSIVE DEVICES

RELATED APPLICATIONS

This application is a continuation in part of Ser. No. 09/189,540, filed Nov. 10, 1998.

FIELD OF THE INVENTION

This invention relates to a medical device for forming an embolism within the vasculature of a patient. More particularly, it is a vaso-occlusion device at least partially coated with a bioactive agent, a collagenous material, or a collagenous coating optionally containing or coated with other bioactive agents. A highly flexible vaso-occlusive device coated with such materials also forms a variation of the invention.

BACKGROUND

Vaso-occlusive devices are surgical implants that are placed within open sites in the vasculature of the human body. The devices are introduced typically via a catheter to the site within the vasculature that is to be closed. That site may be within the lumen of a blood vessel or perhaps within an aneurysm stemming from a blood vessel.

There are a variety of materials and devices which have been used to create such emboli. For instance, injectable fluids such as microfibrillar collagen, various polymeric foams and beads have also been used. Polymeric resins, particularly cyanoacrylate resins, have been used as injectable vaso-occlusive materials. Both the injectable gel and resin materials are typically mixed with a radio-opaque material to allow accurate siting of the resulted material. There are significant risks involved in use of a cyanoacrylates, because of the potential for misplacement. Such a misplacement would create emboli in undesired areas. Cyanoacrylate resins or glues are somewhat difficult, if not impossible, to retrieve once they are improperly placed.

Other available vaso-occlusive devices include mechanical vaso-occlusive devices. Examples of such devices are helically wound coils and braids. Various shaped coils have been described. For example, U.S. Pat. No. 5,624,461, to Mariant, describes a three-dimensional in-filling vaso-occlusive coil. U.S. Pat. No. 5,639,277, to Mariant et al., describes embolic coils having twisted helical shapes and U.S. Pat. No. 5,649,949, to Wallace et al., describes variable cross-section conical vaso-occlusive coils. A random shape is described, as well. U.S. Pat. No. 5,648,082, to Sung et al., describes methods for treating arrhythmia using coils which assume random configurations upon deployment from a catheter. U.S. Pat. No. 5,537,338 describes a multi-element intravascular occlusion device in which shaped coils may be employed. Spherical shaped occlusive devices are described in U.S. Pat. No. 5,645,558 to Horton. Horton describes how one or more strands can be wound to form a substantially hollow spherical or ovoid shape when deployed in a vessel. U.S. Pat. Nos. 5,690,666 and 5,718,711, by Berenstein et al., show a very flexible vaso-occlusive coil having little or no shape after introduction into the vascular space.

There are a variety of ways of discharging shaped coils and linear coils into the human vasculature. In addition to those patents which apparently describe only the physical pushing of a coil out into the vasculature (e.g., Ritchart et al.), there are a number of other ways to release the coil at a specifically chosen time and site. U.S. Pat. No. 5,354,295 and its parent, U.S. Pat. No. 5,122,136, both to Guglielmi et al., describe an electrolytically detachable embolic device. That is to say that a joint between the pusher wire and the vaso-occlusive portion dissolves or erodes when an electrical current is applied to the pusher wire.

A variety of mechanically detachable devices are also known. For instance, U.S. Pat. No. 5,234,437, to Sepetka, shows a method of unscrewing a helically wound coil from a pusher having an interlocking surface. U.S. Pat. No. 5,250,071, to Palermo, shows an embolic coil assembly using interlocking clasps that are mounted both on the pusher and on the embolic coil. U.S. Pat. No. 5,261,916, to Engelson, shows a detachable pusher-vaso-occlusive coil assembly having an interlocking ball and keyway-type coupling. U.S. Pat. No. 5,304,195, to Twyford et al., shows a pusher-vaso-occlusive coil assembly having an affixed, proximately extending wire carrying a ball on its proximal end and a pusher having a similar end. The two ends are interlocked and disengage when expelled from the distal tip of the catheter. U.S. Pat. No. 5,312,415, to Palermo, also shows a method for discharging numerous coils from a single pusher by use of a guidewire which has a section capable of interconnecting with the interior of the helically wound coil. U.S. Pat. No. 5,350,397, to Palermo et al., shows a pusher having a throat at its distal end and a pusher through its axis. The pusher sheath will hold onto the end of an embolic coil and will then be released upon pushing the axially placed pusher wire against the member found on the proximal end of the vaso-occlusive coil.

In addition, several patents describe deployable vaso-occlusive devices that have added materials designed to increase their thrombogenicity. For example, fibered vaso-occlusive devices have been described at a variety of patents assigned to Target Therapeutics, Inc., of Fremont, Calif. Such vaso-occlusive coils having attached fibers is shown in U.S. Pat. Nos. 5,226,911 and 5,304,194, both to Chee et al. Another vaso-occlusive coil having attached fibrous materials is found in U.S. Pat. No. 5,382,259, to Phelps et al. The Phelps et al. patent describes a vaso-occlusive coil which is covered with a polymeric fibrous braid on its exterior surface. U.S. Pat. No. 5,658,308, to Snyder, is directed to a coil having a bioactive core.

In other attempts to increase thrombogenicity, vaso-occlusive coils have also been treated with variety of substances. For instance, U.S. Pat. No. 4,994,069, to Ritchart et al., describes a vaso-occlusive coil that assumes a linear helical configuration when stretched and a folded, convoluted configuration when relaxed. The stretched condition is used in placing the coil at the desired site (via passage through the catheter) and the coil assumes a relaxed configuration—which is better suited to occlude the vessel—once the device is so-placed. Ritchart et al. describes a variety of shapes. The secondary shapes of the disclosed coils include "flower" shapes and double vortices. The coils may be coated with agarose, collagen, or sugar.

U.S. Pat. No. 5,669,931, to Kupiecki, discloses coils that may be filled or coated with thrombotic or medicinal material. U.S. Pat. No. 5,749,894, to Engleson, discloses polymer-coated vaso-occlusion devices. U.S. Pat. No. 5,690,671 to McGurk discloses an embolic element which may include a coating, such as collagen, on the filament surface.

U.S. Pat. No. 5,536,274 to Neuss shows a spiral implant which may assume a variety of secondary shapes. Some complex shapes can be formed by interconnecting two or more of the spiral-shaped implants. To promote blood coagulation, the implants may be coated with metal particles, silicone, PTFE, rubber lattices, or polymers.

None of the above documents discuss vaso-occlusive devices such as those found below, and specifically not the preferred combination vaso-occlusive coils associated with the coating materials in the configuration disclosed herein.

SUMMARY OF THE INVENTION

The invention includes a vaso-occlusive device comprising: a) a biocompatible metal or polymer vaso-occlusive base member or structure, e.g., a coil or braid or aneurysm neck bridge; b) optional fibrous materials attached to the base member; c) an inner optional coating treatment or tie coating on said vaso-occlusive member; d) a collagenous outer coating and/or other natural or synthetic proteins one or more bioactive agents optionally associated with said collagenous outer layer. The vaso-occlusive member may be a coil, a braid, a sphere, or other shaped structure. In a preferred embodiment, the vaso-occlusive member is an elongated helical coil made up of a series of helical windings, for instance a cylindrical helical coil. Preferably, the coil is made of gold, rhenium, platinum, palladium, rhodium, ruthenium, stainless steel, tungsten and alloys, titanium/nickle and alloys thereof.

The optional, inner tie coating is a material suitable for providing a binding layer between the vaso-occlusive device and the outer collagenous or proteinaceous coating. Preferably, the inner coating is bonded to said vaso-occlusive member. The inner coating may be, for instance, of known silane coupling agents or primer polymer agents, e.g., low molecular weight polymer adhesives or the like. The inner coating may also be deposited on the member by plasma treatment or may simply be a plasma treatment of the type intended to etch the substrate. The inner coating may also include vapor-deposited polymers, e.g., polyxyxylene and the like. Other methods for applying the thin polymeric inner coatings, e.g., by dipping or spraying dilute polymeric solution, may also be employed.

The vaso-occlusive device may include polymeric fibers in various configurations, e.g., tufted, looping, braided, etc. which are then coated with the proteinaceous matter.

The outer coating may be proteinaceous, preferably collagenous, in nature and may be applied either as a "neat" or substantially pure layer or may be used as a base or support for or in mixture with other components with a specific role, e.g., genes, growth factors, biomolecules, peptides, oligonucleotides, members of the integrin family, RGD-containing sequences, oligopeptides, e.g., fibronectin, laminin, bitronectin, hyaluronic acid, silk-elastin, elastin, fibrinogen, and other basement membrane proteins with bioactive agents. Preferably, the outer coating comprises a photo-polymerizable collagen or other protein which will bind both with the inner tie layer and with the added bioactive agents.

The invention includes, as a variation, a combination of the vaso-occlusive base member, an inner optional tie coating; collagenous outer coating, and optionally one or more bioactive agents associated with said collagenous outer layer applied to the base member in such a way that they do not substantially affect the physical attributes of the base member, e.g., its flexibility. Preferably, the various coatings do not affect the inherent shape of the vaso-occlusive member after deployment.

The invention further includes, as a variation, a combination of the vaso-occlusive base member, an inner optional tie coating, and one or more bioactive agents applied directly to the base member. Again, such bioactive materials include genes, growth factors, biomolecules, peptides, oligonucleotides, members of the integrin family, RGD-containing sequences, oligopeptides, e.g., fibronectin, laminin, bitronectin, hyaluronic acid, silk-elastin, elastin, fibrinogen, and other basement membrane proteins with bioactive agents.

The invention involves a method for treating a vaso-occlusive device comprising (a) applying an inner tie coating for a vaso-occlusive device; and (b) applying an outer coating over said inner tie coating.

As will become apparent, preferred features and characteristics of one aspect of the invention are applicable to any other aspect of the invention.

DESCRIPTION OF THE INVENTION

Figure 1:
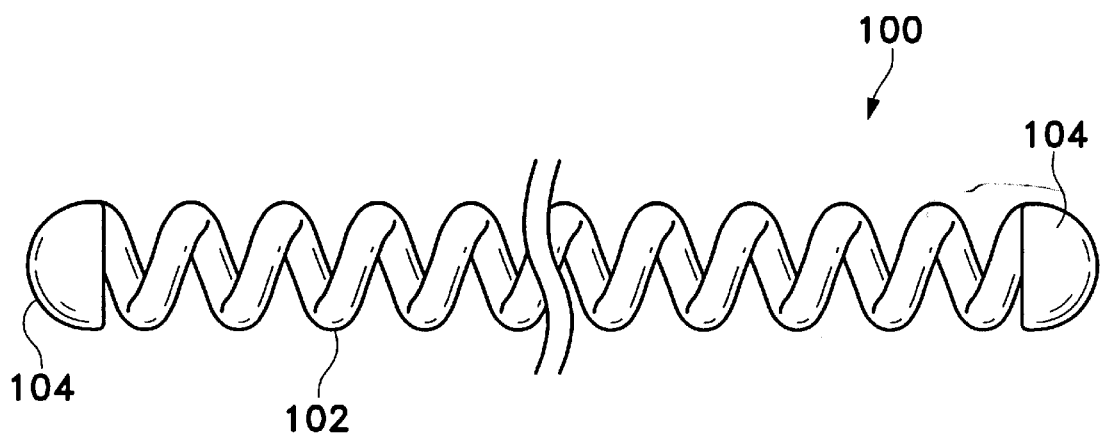
FIG. 1 is a perspective view of one embodiment of the invention.

This invention is a vaso-occlusive device having an outer coating of a collagen-based material or other bioactive material. It may have other functional drugs or proteins associated (chemically linked or physically mixed) with the collagen. The collagen-based material is for the purpose of enhancing the rate and density of the occlusion produced by the vaso-occlusive device at the selected body site and specifically to promote permanent cellular in-growth at that site. The therapeutics, drugs, or proteinaceous material associated with the collagenous material are placed in the collagen to provide specific effects outlined below.

As used, the outer, collagen-based or other bioactive-based coating is preferably placed over an inner tie layer coating or treatment. The binding layer preferably provides a layer contiguous to the vaso-occlusive device and the outer coating. The inner coating is generally bonded to said vaso-occlusive member. The inner coating may be of known silane coupling agents or primer polymer agents (e.g., low molecular weight polymer adhesives) or the like. The inner coating may also be deposited on the member by plasma treatment or may simply be a plasma treatment of the type intended to etch the substrate. The inner coating may also include vapor-deposited polymers, e.g., polyxyxylene and the like. Other methods for applying the thin polymeric inner coatings, e.g., by dipping or spraying dilute polymeric solution, may also be employed.

Preferably, the inner coating is permanently bonded to the coil and either chemically or physically bonded to the outer coating so that shortly after coil deployment, the outer material can safely perform its intended purpose, i.e. beginning the healing cascade within the vessel.

Another suitable tie layer coating involves "plasma treatment" of coils. (See, e.g., co-pending U.S. Ser. No. 08/598, 325). These plasma-treated coils exhibit an amino-functionality which may be measured using known chemical methods. When the devices treated by this process are placed in a bloodstream, the amino-functionality results in a slight positive ionic charge on the surface of the fibers. This amino-functionality attracts platelets and thrombogenic proteins from the bloodstream. Plasma treatment may be carried out using e.g., a plasma generator such as that found in U.S. Pat. No. 3,847,652. The plasma may comprise a nitrogen-containing gas, preferably those containing diatomic nitrogen or ammonia. Gas pressures are advantageously maintained at a very low level, e.g., no greater than about 5 millimeters of mercury, preferably from 0.1 to 2 millimeters of mercury.

The period of time in which the vaso-occlusive device is subjected to the plasma need not be great. That is to say that for most applied power settings below about 200 watts and in the radio frequency region between 1 and 50 megaHertz, the time of reaction need not be greater than 10 minutes to achieve the result described herein.

Other plasma treating steps which are intended to etch the substrate are also suitable for this invention.

Figure 2:
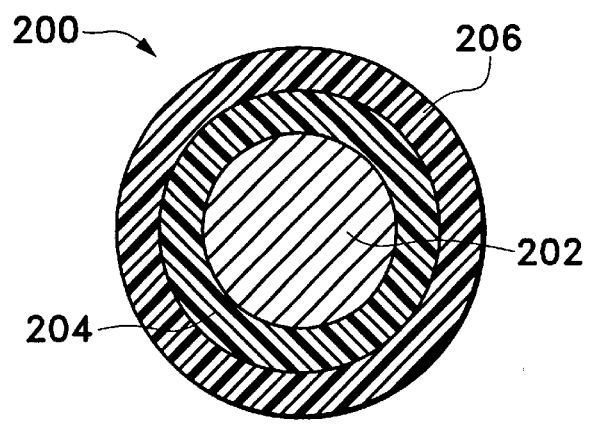
FIG. 2 is a perspective view of another embodiment of the invention showing a coil having a permanently bonded inner coating of a thrombotic agent and a water-soluble, dissolvable outer coating of an anti-thrombotic agent.

FIGS. 1 and 2 show typical vaso-occlusive devices suitable for use with this procedure. FIG. 1 shows a typical vaso-occlusive device (100). Vaso-occlusive device (100) is shown in FIG. 1 to include a helically wound coil (102) having tips (104) to ease the potential of the component wire to cause trauma in a blood vessel. The device may include tufts or fiber bundles attached to it, so to increase the amount and volume of fiber held by the coil and thereby to promote overall thrombogenicity of the device. Typical of a vaso-occlusive device comprising a helical coil having attached fibrous elements such as shown in FIG. 1 is found in U.S. Pat. No. 5,226,911, to Chee et al, the entirety of which is incorporated by reference.

FIG. 2 shows a vaso-occlusive device (200) comprising a helically wound coil (202), an inner tie coating (204) and an outer collagenous coating (206). The inner coating is generally a substance, preferably proteinaceous, which is bound to the coil (202) and which is also bound, physically or chemically, to the outer collagenous covering (206).

The occlusion devices of the invention may be made using conventional equipment and procedures. For example, helical coils may be prepared by wrapping a suitable wire about a cylindrical or conical mandrel. The strand(s) are then placed axially through the core of the helix and, if a multiplicity of strands are employed, their ends may be bound by heat, adhesives, or mechanical means. Radial filaments may be attached to the windings of the helix by tying or with adhesives.

The polymeric materials used in the vaso-occlusive devices in FIGS. 1 and FIG. 2 are known materials. They are those materials which are generally approved for use as implants in the body or could be so approved. They may be of polymers such as polyethylene, polyacrylics, polypropylene, polyvinylchloride, polyamides such as Nylon, polyurethanes, polyvinylpyrrolidone, polyvinyl alcohols, polyvinylacetate, cellulose acetate, polystyrene, polytetrafluoroethylene, polyesters such as polyethylene terephthalate (Dacron), silk, cotton, and the like. When the polymers are fibrous, they are often looped or tufted as shown in the drawings. Although it is not critical to this invention, they are usually assembled in bundles of 5 to 100 fibers per bundle. Preferred materials for the polymer component of vaso-occlusive devices comprise polyesters, polyethers, polyamides, and polyfluorocarbons. Especially preferred is polyethyleneterephthalate, sold as Dacron. Placing a protein-based covering on the fibers is a variation of the invention.

Another variation of the invention includes the specific use of polymers which evince an angiogenic response, preferably, biodegradable polymers, that are associated with the vaso-occlusive support base. By "associated" is meant that the material is tied to or is made to adhere to the vaso-occlusive support base. The composition may be a fabric or gauze-like structure. It may also be a non-woven or loose agglomeration of individual fibers. In general, they need to stay in place during the placement of the device in the body.

Preferably, the associated covering is a polymeric material such as a biodegradable polymer, e.g., polyglycolic acid, polylactic acid, reconstituted collagen, poly-p-dioxanone, and their copolymers such as poly(glycolide-lactide) copolymer, poly(glycolide-trimethylene carbonate) copolymer, poly(glycolide-ε-caprolactone) copolymer, glycolide-trimethylene carbonate triblock copolymer, and the like. Mixtures of the noted polymers, e.g., of polylactide and polyglycolide may also be used. The associated coverings may also be used in conjunction with the bioactive coatings discussed elsewhere.

The coils (102 in FIG. 1 and 202 in FIG. 2) may be made of any of a wide variety of biocompatible metals or polymers or carbon. In particular, the metals may be selected from gold, rhenium, platinum, palladium, rhodium, ruthenium, various stainless steels, tungsten, and their alloys, titanium/nickle alloys particularly nitinoltype alloys. The preferred alloy is one comprising upwards of 90 percent platinum and at least a portion of the remainder, tungsten. This alloy exhibits excellent biocompatibility and yet has sufficient strength and ductility to be wound into coils of primary and secondary shape and will retain those shapes upon placement of the vaso-occlusive device in the human body. The diameter of the wire typically making up the coils is often in a range of 0.005 and 0.050 inches. The resulting primary coil diameter typically is in the range of 0.008 and 0.085 inches. Smaller coil diameters are used for finer problems and larger coil diameters and wire diameters are used in larger openings in the human body. A typical coil primary diameter is 0.015 and 0.018 inches. The axial length of a vaso-occlusive device may be between 0.5 and 100 centimeters. The coils are typically wound to have between 10 and 75 turns per centimeter.

In addition to the coils shown in the Figures, the vaso-occlusive device may comprise a substrate comprising a woven braid rather than the helical coil shown in those Figures. The vaso-occlusive device may comprise a mixture of coil and braid. Indeed, it is within the scope of this invention that a portion of the coil be polymeric or a combination of metal and polymer.

It is further within the scope of this invention that the vaso-occlusive device comprise shapes or structures other than coils or braids, for examples, spherical structures and the like.

In one aspect of the present invention, the vaso-occlusive devices described above and those similar to those specifically described above, are first optionally treated with a tie layer coating and then subjected to treatment to provide the outer collagenous, proteinaceous, or bioactive material layer. Preferably, neither the inner nor outer coatings interfere with the shape of the coil after deployment. In one variation of the invention, the outer layer is applied to the vaso-occlusive base without the inner tie layer, but is applied in such an amount that the resulting assembly is not significantly more stiff than is the vaso-occlusive device without the covering. That is to say, the coated device is not more than 35%, preferably not more than 15%, and most preferably not more than 5%, stiffer than is the untreated device base. Preferably, the covering is less than about 1.0 mil, more preferably less than about 0.5 mil in thickness.

When a collagen layer, the outer collagenous layer may be of a wide variety of types, natural or synthetic, but preferably comprises a photo-polymerizable collagen which will bind both with the inner tie layer and with the added bioactive agents. The preferred collagenous materials have the same surface functional groups as do Type I and Type IV natural collagens. Those functional groups are typically of the type which bind to acrylate-type linkages.

The outer collagenous or proteinaceous coating may further contain additional materials which have one or more functions, including, but not limited to, reducing friction, providing a therapeutic for local or blood borne delivery, or enhancing thrombosis, coagulation, or platelet activity. The additional materials may be applied either as a substantially pure layer over the collagenous layer or chemically bonded to (and interspersed with) the collagenous layer or physically bonded to the outer collagenous layer The added bio-active materials may be, e.g., genes, growth factors, biomolecules, peptides, oligonucleotides, members of the integrin family, RGD-containing sequences, oligopeptides, e.g., fibronectin, laminin, vitronectin, hyaluronic acid, silk-elastin, elastin, fibrogenin, and other basement membrane proteins with bioactive agents.

Non-limiting examples of bioactive coatings or materials suitable in this invention include both natural and synthetic compounds, e.g., fibrinogen, other plasma proteins, growth factors (e.g., vascular endothelial growth factor, "VEGF"), synthetic peptides of these and other proteins having attached RGD (arginine-glycine-aspartic acid) residues generally at one or both termini, or other cell adhesion peptides, i.e., GRGDY, oligonucleotides, full or partial DNA constructs, natural or synthetic phospholipids, or polymers with phosphorylcholine functionality.

Other bioactive materials which may be used in the present invention include, for example, pharmaceutically active compounds, proteins, oligonucleotides, ribozymes, anti-sense genes, DNA compacting agents, gene/vector systems (i.e., anything that allows for the uptake and expression of nucleic acids), nucleic acids (including, for example, naked DNA, cDNA, RNA, DNA, cDNA or RNA in a non-infectious vector or in a viral vector which may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic polymers that are selected from a number of types depending on the desired application, including retrovirus, adenovirus, adeno-associated virus, herpes simplex virus, and the like. For example, biologically active solutes include anti-thrombogenic agents such as heparin, heparin derivatives, urokinase, PPACK (dextrophenylalanine proline arginine chloromethylketone), rapamycin, probucol, and verapimil; angiogenic and anti-angiogenic agents; anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-mitotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Arg chloromethyl keton, an RGD peptide-containing compound, heparin, antithrombin compounds, platelet receptor antagonists, anti-thrombin anticodies, anti-platelet receptor antibodies, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directly against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms, and combinations thereof. These and other compounds are applied to the stenting device.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic polypeptides. A polypeptide is understood to be any translation production of a polynucleotide regardless of size, and whether glycosylated or not. Therapeutic polypeptides include as a primary example, those polypeptides that can compensate for defective or deficient species in an animal, or those that act through toxic effects to limit or remove harmful cells from the body. In addition, the polypeptides or proteins that can be incorporated into the polymer coating 130, or whose DNA can be incorporated, include without limitation, proteins competent to induce angiogenesis, including factors such as, without limitation, acidic and basic fibroblast growth factors, vascular endothelial growth factor (including VEGF-2, VEGF-3, VEGF-A, VEGF-B, VEGF-C) hif-1 and other molecules competent to induce an upstream or downstream effect of an angiogenic factor; epidermal growth factor, transforming growth factor $\alpha$ and $\beta$, platelet-derived endothelial growth factor, platelet-derived growth factor, tumor necrosis factor $\alpha$, hepatocyte growth factor and insulin like growth factor; growth factors; cell cycle inhibitors including CDK inhibitors; thymidine kinase ("TK") and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

In one exemplary embodiment of the present invention, the medical device has recombinant nucleic acid incorporated therein, wherein the recombinant nucleic acid comprises a viral vector having linked thereto an exogenous nucleic acid sequence. "Exogenous nucleic acid sequence" is used herein to mean a sequence of nucleic acids that is exogenous to the virus from which the vector is derived. The concentration of the viral vector, preferably an adenoviral vector, is at least about $10^{10}$ plaque forming units ("p.f.u."), preferably at least about $10^{11}$ p.f.u. Alternatively, the concentration of the viral vector is limited by the concentration that results in an undesirable immune response from a patient.

Treatment of vaso-occlusive coils with the described materials may be carried out using known methods, for example dip coating, spray coating, wiping, vapor deposition or the like.

The devices that are treated according to the procedure of this invention are often introduced to a selected site using the procedure outlined below. This procedure may be used in treating a variety of maladies. For instance, in treatment of an aneurysm, the aneurysm itself may be filled with the devices made according to the procedure specified here. Shortly after the devices are placed within the aneurysm, an emboli begins to form and, at some later time, is at least partially replaced by cellular material formed around the vaso-occlusive devices.

In general, a selected site is reached through the vascular system using a collection of specifically chosen catheters and guide wires. It is clear that should the aneurysm be in a remote site, e.g., in the brain, methods of reaching this site are somewhat limited. One widely accepted procedure is found in U.S. Pat. No. 4,994,069 to Ritchart, et al. It utilizes a fine endovascular catheter such as is found in U.S. Pat. No. 4,739,768, to Engelson. First of all, a large catheter is introduced through an entry site in the vasculature. Typically, this would be through a femoral artery in the groin. Other entry sites sometimes chosen are found in the neck and are in general well known by physicians who practice this type of medicine. Once the introducer is in place, a guiding catheter is then used to provide a safe passageway from the entry site to a region near the site to be treated. For instance, in treating a site in the human brain, a guiding catheter would be chosen which would extend from the entry site at the femoral artery, up through the large arteries extending to the heart, around the heart through the aortic arch, and downstream through one of the arteries extending from the upper side of the aorta. A guidewire and neurovascular catheter such as that described in the Engelson patent are then placed through the guiding catheter as a unit. Once the tip of the guidewire reaches the end of the guiding catheter, it is then extended using fluoroscopy, by the physician to the site to be treated using the vaso-occlusive devices of this invention. During the trip between the treatment site and the guide catheter tip, the guidewire is advanced for a distance and the neurovascular catheter follows. Once both the distal tip of the neurovascular catheter and the guidewire have reached the treatment site, and the distal tip of that catheter is appropriately situated, e.g., within the mouth of an aneurysm to be treated, the guidewire is then withdrawn. The neurovascular catheter then has an open lumen to the outside of the body. The devices of this invention are then pushed through the lumen to the treatment site. They are held in place variously because of their shape, size, or volume. These concepts are described in the Ritchart et al patent as well as others. Once the vaso-occlusive devices are situated in the vascular site, the embolism forms.

Modifications of the procedure and device described above, and the methods of using them in keeping with this invention will be apparent to those having skill in this mechanical and surgical art. These variations are intended to be within the scope of the claims that follow.

We claim as our invention:

1. A vaso-occlusive device comprising:
   a) a vaso-occlusive member;
   b) an inner coating on at least a portion of said vaso-occlusive member, said inner coating being free from protein; and
   c) a protein-based outer coating on said inner coating wherein said inner coating is not applied by plasma treatment.

2. The device of claim 1 wherein the protein-based outer coating is collagen-based.

3. The device of claim 1 wherein the vaso-occlusive member is a metallic element comprising an elongated helical coil.

4. The device of claim 3 wherein the coil is a cylindrical helical coil.

5. The device of claim 3 wherein the coil comprises a metal selected from gold, rhenium, platinum, palladium, rhodium, ruthenium, stainless steel, tungsten, titanium, nickel, and alloys thereof.

6. The device of claim 1 wherein the inner coating is a polymer-based agent.

7. The device of claim 6 wherein the inner coating is bonded to said vaso-occlusive member.

8. The device of claim 7 wherein the inner coating is applied by a procedure selected from the group consisting of applying a silane coupling agent, applying a acrylate-based coupling agent, applying a low molecular weight adhesive agent, vapor deposition, and polymer coating from a dilute solution.

9. The device of claim 1 wherein said outer coating is photo-polymerizable.

10. The device of claim 8 wherein the inner coating is paraxyxylene and deposited by vapor deposition.

11. The device of claim 1 further comprising a bioactive material selected from the group consisting of genes, growth factors, biomolecules, peptides, oligonucleotides, members of the integrin family, RGD-containing sequences, oligopeptides, e.g., fibronectin, laminin, vitronectin, hyaluronic acid, silk-elastin, elastin, infibrogen, and other basement membrane proteins with bioactive agents.

12. The device of claim 11 wherein said bioactive material is a coating on said protein-based outer coating.

13. The device of claim 11 wherein said bioactive material is intermixed with said protein-based outer coating.

14. A vaso-occlusive device comprising:
   a) a vaso-occlusive member, and
   b) an inner material on at least a portion of said vaso-occlusive member, said inner material being free from protein; and
   c) a protein-based outer coating on said inner material wherein said inner material is not applied by plasma treatment.

15. The device of claim 14 wherein the protein-based outer coating is collagen-based.

16. The device of claim 14 wherein the vaso-occlusive member is a metallic element comprising an elongated helical coil.

17. The device of claim 16 wherein the coil is a cylindrical helical coil.

18. The device of claim 17 wherein the coil comprises a metal selected from gold, rhenium, platinum, palladium, rhodium, ruthenium, stainless steel, tungsten, titanium, nickle, and alloys thereof.

19. The device of claim 14 wherein said outer coating is photo-polymerizable.

20. The device of claim 14 further comprising a bioactive material selected from the group consisting of genes, growth factors, biomolecules, peptides, oligonucleotides, members of the integrin family, RGD-containing sequences, oligopeptides, e.g., fibronectin, laminin, vitronectin, hyaluronic acid, silk-elastin, elastin, infibrogen, and other basement membrane proteins with bioactive agents.

21. The device of claim 14 further comprising fibrous material attached to the vaso-occlusive member that is also at least partially covered by said protein-based outer coating.

22. The device of claim 21 wherein said inner material is an adhesive.

23. The device of claim 21 wherein said fibrous material is a gauze.

24. The device of claim 23 wherein said inner material is an adhesive.

25. The device of claim 17 further comprising fibrous material attached to the vaso-occlusive member that is also at least partially covered by said protein-based outer coating.

26. The device of claim 25 wherein said fibrous material comprises one or more polymers.

27. The device of claim 26 wherein said one or more polymers is selected from the group consisting of polyglycolic acid, polylactic acid, reconstituted collagen, poly-p-dioxanone, and their copolymers such as poly(glycolide-lactide) copolymer, poly(glycolide-trimethylene carbonate) copolymer, poly(glycolide-ε-caprolactone) copolymer, glycolide-trimethylene carbonate triblock copolymer, and mixtures.

28. The device of claim 27 wherein said protein-based outer coating contains materials for reducing friction.

29. A vaso-occlusive device comprising:

a) a vaso-occlusive member having a flexibility; and b) an inner material on at least a portion of said vaso-occlusive member, said inner material being free from protein; and c) a protein-based outer coating on said inner material in such amount and thickness that the flexibility of the vaso-occlusive device is not more than 35% stiffer than said vaso-occlusive member wherein said inner material is not applied by plasma treatment.

30. The device of claim 29 wherein the protein-based outer coating is collagen-based.

31. The device of claim 30 wherein the vaso-occlusive device is not more than 10% stiffer than said vaso-occlusive member.

32. The device of claim 29 wherein the vaso-occlusive member is a metallic element comprising an elongated helical coil.

33. The device of claim 32 wherein the coil is a cylindrical helical coil.

34. The device of claim 32 wherein the coil comprises a metal selected from gold, rhenium, platinum, palladium, rhodium, ruthenium, stainless steel, tungsten, titanium, nickle, and alloys thereof.

35. The device of claim 29 wherein said outer coating is photo-polymerizable.

36. The device of claim 29 further comprising fibrous material attached to the vaso-occlusive member that is also at least partially covered by said protein-based outer coating.

37. The device of claim 29 further comprising a bioactive material selected from the group consisting of genes, growth factors, biomolecules, peptides, oligonucleotides, members of the integrin family, RGD-containing sequences, oligopeptides, e.g., fibronectin, laminin, bitronectin, hyaluronic acid, silcolastin, fibrogenin, and other basement proteins with bioactive agents.

38. The device of claim 37 wherein said bioactive material is a coating.

39. The device of claim 37 wherein said bioactive material is intermixed with said protein-based coating.

40. The device of claim 36 wherein said fibrous material comprises one or more polymers.

41. The device of claim 40 wherein said one or more polymers is selected from the group consisting of polyglycolic acid, polylactic acid, reconstituted collagen, poly-p-dioxanone, and their copolymers such as poly(glycolide-lactide) copolymer, poly(glycolide-trimethylene carbonate) copolymer, poly(glycolide-ε-caprolactone) copolymer, glycolide-trimethylene carbonate triblock copolymer, and mixtures.

42. A vaso-occlusive device comprising:

a) a vaso-occlusive member;

b) an inner coating on at least a portion of said vaso-occlusive member, said inner coating being free from protein; and c) a bioactive-material-based outer coating on said inner coating wherein said inner coating is not applied by plasma treatment.

43. The device of claim 42 wherein the vaso-occlusive member is a metallic element comprising an elongated helical coil.

44. The device of claim 42 wherein the coil is a cylindrical helical coil.

45. The device of claim 44 wherein the coil comprises a metal selected from gold, rhenium, platinum, palladium, rhodium, ruthenium, stainless steel, tungsten, titanium, nickle, and alloys thereof.

46. The device of claim 42 wherein the inner coating is applied by a procedure selected from the group consisting of applying a silane coupling agent, applying a acrylate-based coupling agent, applying a low molecular weight adhesive agent, vapor deposition, and polymer coating from a dilute solution.

47. The device of claim 46 wherein the inner coating is paraxyxylene and deposited by vapor deposition.

48. The device of claim 42 wherein the bioactive material is selected from the group consisting of genes, growth factors, biomolecules, peptides, oligonucleotides, members of the integrin family, RGD-containing sequences, oligopeptides, e.g., fibronectin, laminin, vitronectin, hyaluronic acid, silk-elastin, elastin, infibrogen, and other basement membrane proteins with bioactive agents.

* * * * *